(12) United States Patent  (10) Patent No.: US 7,932,091 B2
Keister  (45) Date of Patent: Apr. 26, 2011

(54) COLORANT TRACER FOR COOLING WATER TREATMENT FORMULATIONS

(75) Inventor: Timothy Keister, Brockway, PA (US)

(73) Assignee: ProChemTech International, Inc., Brockway, PA (US)

( * ) Notice: Subject to any disclaimer, the term of this patent is extended or adjusted under 35 U.S.C. 154(b) by 330 days.

(21) Appl. No.: 11/700,643

(22) Filed: Jan. 31, 2007

(65) Prior Publication Data

US 2008/0020470 A1    Jan. 24, 2008

Related U.S. Application Data

(60) Provisional application No. 60/831,344, filed on Jul. 18, 2006.

(51) Int. Cl.
   *G01N 35/08*    (2006.01)
   *G01N 21/00*    (2006.01)

(52) U.S. Cl. ....... 436/55; 210/764; 252/387; 252/389.1; 436/56; 436/164

(58) Field of Classification Search ............ 436/56
   See application file for complete search history.

(56) References Cited

U.S. PATENT DOCUMENTS

| | | | |
|---|---|---|---|
| 4,783,314 A | 11/1988 | Hoots et al. | |
| 4,992,380 A | 2/1991 | Moriarty et al. | |
| 5,120,661 A * | 6/1992 | Baker et al. | 436/164 |
| 5,171,450 A | 12/1992 | Hoots | |
| 5,229,842 A | 7/1993 | Dolan et al. | |
| 5,266,493 A | 11/1993 | Young | |
| 5,278,074 A | 1/1994 | Rao et al. | |
| 5,416,323 A | 5/1995 | Hoots et al. | |
| 5,435,969 A | 7/1995 | Hoots et al. | |
| 5,858,798 A | 1/1999 | Godfrey et al. | |
| 5,998,632 A | 12/1999 | Ward et al. | |
| 6,153,110 A | 11/2000 | Richardson et al. | |
| 6,255,118 B1 | 7/2001 | Alfano et al. | |
| 6,280,635 B1 | 8/2001 | Moriarty et al. | |
| 6,369,894 B1 | 4/2002 | Rasimas et al. | |
| 6,585,933 B1 | 7/2003 | Ehrhardt et al. | |
| 6,685,840 B2 | 2/2004 | Hatch | |
| 6,750,328 B1 | 6/2004 | Wetegrove et al. | |
| 6,966,213 B2 | 11/2005 | Hoots et al. | |
| 2002/0131941 A1 * | 9/2002 | Habeck et al. | 424/63 |
| 2003/0127341 A1 * | 7/2003 | King et al. | 205/788.5 |

(Continued)

FOREIGN PATENT DOCUMENTS

EP    541318 A1 *    5/1993

*Primary Examiner* — Krishnan S Menon
*Assistant Examiner* — Dirk Bass
(74) *Attorney, Agent, or Firm* — Kilyk & Bowersox, P.L.L.C.

(57) ABSTRACT

Water-based colorant traced formulations (products) containing one or more water treatment agents, such as phosphonates, polyacrylic acids and/or polymers, co-polymers, terpolymers thereof, azoles, molybdate, polysilicates, phosphates, zinc, polyphosphates, etc., are provided wherein the water-soluble colorant is detectable in the visible light range of about 580-640 nm and is chemically inert relative to the water treatment agent(s). Measurement of an optical property of the colorant in the treated coolant water permits the concentration of the product therein to be ascertained, and the level of the product containing can be adjusted for controlling scale, corrosion, deposition, and/or microbial activity in commercial and/or industrial cooling water systems. These products may be reliably monitored and dosed to maintain a product level in treated water of 5 to 500 mg/L.

19 Claims, 1 Drawing Sheet

U.S. PATENT DOCUMENTS

Figure 1:
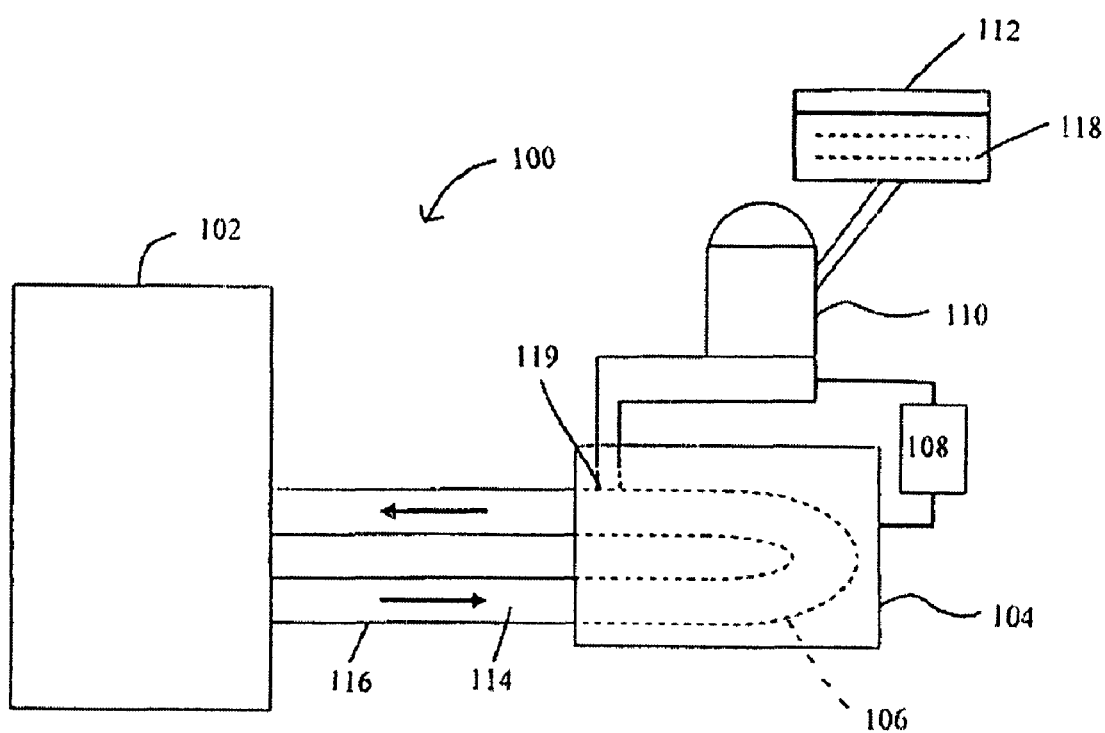

| | | |
|---|---|---|
| 2003/0141258 A1 | 7/2003 | Hatch |
| 2004/0055965 A1* | 3/2004 | Hubig et al. .................. 210/748 |
| 2005/0242042 A1 | 11/2005 | Moriarty et al. |
| 2006/0054564 A1 | 3/2006 | Woyciesjes et al. |
| 2006/0160226 A1 | 7/2006 | Johnson |
| 2006/0160227 A1 | 7/2006 | Sethumadhavan et al. |
| 2006/0246595 A1 | 11/2006 | Banks et al. |

* cited by examiner

COLORANT TRACER FOR COOLING WATER TREATMENT FORMULATIONS

CROSS-REFERENCE TO RELATED APPLICATIONS

This application claims benefit of priority to U.S. Provisional Application No. 60/831,344, filed Jul. 18, 2006, which is hereby incorporated by reference in its entirety.

FIELD

The present invention pertains to use of colorants in compositions and products to enable testing and/or control of the product dosage in cooling water systems.

BACKGROUND

Products containing various organic and/or inorganic additives (actives) have been formulated for control of scale, corrosion, and deposition in commercial and industrial cooling water systems for many years. For example, many products commonly incorporated actives such as phosphate, zinc, and/or molybdate. These actives are used in field testing for control of product dosage, due to ready availability of quick, accurate, test methods.

Recent environmental restrictions on discharge of some actives, such as phosphate, zinc, and molybdate, as well as increased cost for molybdate, have restricted or eliminated such practice. In the case of molybdate, for example, the cost has increased from about $3.00/lb in 2003 to about $14.50/lb in 2005.

A second trend is the use of higher performance phosphonates, copolymers, and terpolymers, in products to enable the cooling water systems to be operated at higher cycles of concentration to minimize water use and discharge. Obtaining accurate field tests on these products using these components has become problematic. Therefore, these higher performance components currently have no usable field test or automatic control procedures, which can be used for control of dosage.

One response to this set of problems has been the development of fluorescent tracers, which are added to the products as a component specifically to allow field testing with subsequent manual or automatic control of dosage. Such technology is disclosed, for example, in U.S. Pat. Nos. 5,998,632 and 6,255,118. Further activity in this field is described in U.S. Pat. No. 6,750,328 B, where use of antibodies for detection of water treatment polymers is disclosed.

Problems associated with prior usages of an organic colorant as a tracer in cooling water formulations include: reactivity with actives in the product formulation; reactivity with stabilizers in the product formulation such as excess acid or caustic; stability towards halogens used to control biological growth in cooling water systems; stability towards non-oxidizing biocides used to control biological growth in cooling water systems; non-reactivity towards common constituents of cooling waters; detectability at low levels by low cost test methods; reasonable colorant unit cost; and so forth.

Therefore, there has been a need for solutions to such problems and shortcomings associated with prior use of water treatment compositions for cooling water systems.

SUMMARY

The present invention is directed to a unique composition, manufacturing method, testing method, and method of use of cooling water treatment agents, that comprise or comprise the use of scale inhibitors, corrosion inhibitors, deposition inhibitors, and/or microbial inhibitors, traced with colorants.

According to various embodiments, a cooling water treatment composition (product) comprises a cooling water system water treatment agent and a water-soluble colorant detectable in a prescribed visible-light spectral range. The cooling water system water treatment agent is selected from a scale inhibitor, a corrosion inhibitor, a deposition inhibitor, a biological organism inhibitor, or a combination thereof. The water-soluble colorant is detectable in visible-light at from about 580 nm to about 640 nm and is chemically inert relative to the water treatment agent(s).

According to various embodiments, the colorant is a tri- and/or tetra-hydrophilic group, substituted copper porphyrin or salt thereof, such as, e.g., sodium tetrasulfonated copper phthalocyanine, which may be formulated with water treatment compositions according to various embodiments of the present invention. The water treatment composition can be either basic or acidic, and can comprise, for example, water treatment compositions having pH values at or above 9.0. In some embodiments, the colorant can comprise triphenylmethane, which can be formulated with water treatment compositions for example, having a pH of below 9.

It has been discovered that such product compositions of the present invention are an improvement over existing technologies as the presence of the colorant in the product permits easy field testing and subsequent manual or automatic control of the product with a minimal increase in product cost, amongst other advantages and benefits. Also, the colorant can be detectable in visible light without the need for a dedicated excitation source.

In other embodiments, the present invention is also directed to methods of using the product compositions in treatment of water cooling systems. The colorant level in the treated water is determined by a simple, accurate absorbance spectrophotometer test to control dosage of the water treatment composition or product in a water cooling system by either manual or automatic addition to maintain desired control levels thereof.

DRAWINGS

FIG. 1 is a schematic diagram of a system, according to various embodiments of the present teachings and used for spectral monitoring and adjusting dosage levels of a water treatment composition comprising a visible light-detectable colorant, in a coolant system.

DETAILED DESCRIPTION

The present teachings relate to a product, also occasionally referred to herein as a composition or formulation, and methods of its use in controlling scale, corrosion, deposition, and/or biological organisms, in cooling water systems. The product comprises a colorant that is detectable in the visible-light range, and preferably in the wavelength range of from about 560 nm to about 660 nm, for example, from about 580 nm to 640 nm. The colorant can be chemically inert and stable with regard to the treatment agent(s) and cooling water. That is, for example, the colorant should not chemically react or interact with or physically attach to the treatment agent(s) to form new or combined entities that have different optical properties than the original colorant. The presence of the colorant can optically be detectable with the naked eye (i.e., without optical magnification in ambient visible light). The colorant also can be instrumentally detected with commercially available, inexpensive, spectrometers (also, occasionally referred to herein interchangeably as spectrophotometers), which can detect visible light in the ranges used according to various embodiments of the present teachings.

Measurement of an optical property, such as absorption, of the colorant at a visible light wavelength in treated coolant permits the concentration of the product therein to be ascertained in real-time and on-site, for example, by using a pre-developed calibration model for a relationship between concentration and the optical property. The level of the product containing the colorant in the treated water then can be adjusted, as desired or needed, to change the concentration of the treatment product to achieve a desired level. Generally, these products may be reliably monitored and dosed to maintain a product level in treated coolant of from about 1 mg/L to about 1000 mg/L, for example, from about 5 mg/L to about 500 mg/L, although other concentrations can be desirably achieved.

Coolant Treatment Compositions (Products)

The coolant treatment product or compositions according to various embodiments of the present teachings can have the following components and features. Unless indicated otherwise, all amounts, percentages, ratios, and the like, described herein, are by weight.

According to various embodiments, the colorants can be particularly suitable for use in alkaline treatment agents that is, treatment agents having a final product pH exceeding about 9.0. In other embodiments, the colorants can be particularly suitable for use in acidic treatment agents, that is, agents having a final product pH of below about 6.0. According to various embodiments, the colorant can be suitable for use with acidic, alkaline, and/or neutral treatment agents.

According to various embodiments, the present teachings encompass colorants that can be used with cooling water treatment agents having one or more of the following characteristics: no reactivity with actives or stabilizers in many varied product formulations; no reactivity with halogens used to control biological growth in cooling water systems; no reactivity with various non-oxidizing biocides used to control biological growth in cooling water systems; no reactivity with common constituents of cooling waters such as calcium, magnesium, alkalinity, chloride, sulfate, silicate, phosphate, iron, copper, zinc, and suspended solids of various kinds, for example, over a pH range of from about 6.0 to about 10.5; easy detection and accurate quantification at low levels by low cost test methods; reasonable colorant cost and availability; stability for a reasonable period in cooling water, to include stability against degradation by sunlight, degradation by oxygen, and degradation by biological activity; non-toxicity including a low toxicity to people and animals; an acceptable coloration of the cooling water by the product; and no absorbance interference with other commonly used cooling water treatment chemicals or products.

According to various embodiments, the colorant can comprise, for example, Turquoise 8 GL (or NFBL), available from American Dyestuff Corporation, Clifton, N.J. The visible light-detectable colorant can be a sodium salt of quad sulphonated copper phthalocyanine. The colorant can have the chemical formula $Na_4C_{32}N_8CuO_{12}S_4$. The colorant can be manufactured by reacting commercial mono- and di-sulphonated copper phthalocyanine, CAS 1330-38-7, to add more sulfoxy groups to the phthalocyanine moiety. For example, the colorant can be produced by reacting a mono- and/or di-sulphonated copper phthalocyanine, such as commercially obtained Direct Turquoise Blue 86 (available from MacDyeChem Industries, Ahmedadad, India, with sulfonic acid. It has been determined that in the Color Index, such a product is called acid blue 249, and assigned a Color Index number of CI 74220. This colorant is available in high purity powder form, although not limited thereto.

Water solubility of mono- and di-sulphonated species of copper phthalocyanine can be increased to a suitable level for water treatment applications by increasing the number of hydrophilic groups on the phthalocyanine moiety, such as in the manner described above. Although exemplified above as sulfoxy, the hydrophilic group(s) introduced for this purpose is not necessarily limited thereto, and comprise a carboxy moiety, a haloalkyl moiety, or other hydrophilic moieties that can increase water solubility of the substituted or functionalized phthalocyanine moiety. Other substituents can optionally be present on the phthalocyanine moiety to the extent they do not destabilize or remove the relevant visible-light detection attributes of the colorant, and preferably do not render the colorant reactive to any water treatment agents.

Also, while a copper phthalocyanine molecule (i.e., copper tetrabenzotetraazaporphyrin) is exemplified herein as a visible light-detectable colorant, according to various embodiments the colorant can comprise a metal porphyrin compound, for example, a copper porphyrin compound having the visible light detectability attributes described herein. For instance, the colorant, in various embodiments, can comprise a water-soluble, visible-light detectable, multi-hydrophilic group-substituted copper porphyrin, or salt thereof. In some embodiments, the colorant is selected from the group consisting of a tri-hydrophilic group-substituted copper porphyrin or salt thereof, a tetra-hydrophilic group-substituted copper porphyrin or salt thereof, and combinations thereof, wherein each hydrophilic group can independently be selected from the group consisting of sulfoxy, carboxy, and haloalkyl groups.

According to other embodiments, the colorant can comprise triphenylmethane colorant, such as Acid Blue 9, CAS 3844-45-9, having the chemical formula $Na_2C_{37}H_{36}N_2O_9S_3$ and commercially available from several suppliers, for example, from Abbey Color™, Philadelphia, Pa., as "ABCOL Acid Blue 9™ Powder" which has Color Index number 42090. This colorant is available in high purity powder form, although not limited thereto.

In formulating the water treatment composition or product, the colorant can be used in combination with one or more water treatment agents selected from scale inhibitors, corrosion inhibitors, deposition inhibitors, and/or biological inhibitors (i.e., biocides or antimicrobials). These water treatment agents can impart a single or multiple performance attribute in the treated coolant water.

According to various embodiments, chemical scale inhibitors that can be used include, for example, polyacrylates, phosphonates, chelants, dipolymers, terpolymers, polyphosphates, combinations thereof, and the like. Deposition inhibitors that can be used include, for example, polyacrylates, polymaleics, dipolymers, terpolymers, polydiols, ethoxylates, sulfonates, combinations thereof, and the like. Non-limiting examples of exemplary polyacrylates include polyacrylic acids selected from polyacrylic acid, polyacrylic acid copolymer, polyacrylic acid terpolymer, and combinations thereof. Non-limiting examples of these phosphonates include, for example, phosphonic acids selected from AMP phosphonic acid, HEDPA phosphonic acid, PBCT phosphonic acid, and combinations thereof. Corrosion inhibitors that can be used include, for example, chromates, molybdates, polysilicates, phosphonate-phosphates, azoles, polydiols, and the like. Particular azoles that can be used can include, for example, a tolytriazole compound, a benzotriazole compound, a mercaptobenzothiazole compound, and combinations thereof. Biocides that may be used include, for example, oxidizing biocides such as bromochlorodimethylhydrantoin, chlorine dioxide, chlorine, ozone, hypochlorite, hypobromite, and/or non-oxidizing biocides such as hydroxymethyl nitro propanediol (Trisnitro), methylene bisthiocyanate (MBT), Quats and Polyquats, carbamates, isothiazolin, glutaraldehyde, and dibromo nitrilo propionamide (DBNPA). Common dosing levels used for these various water treatment agents are generally known.

According to various embodiments, the colorant can be used, for example, in combination with one or more of the following cooling water treatment agents: AA/AMPS polyacrylic copolymer (an acrylic-acrylamide/sulfonic (AMPS) copolymer); Polyacrylic acid, (2000 mw in daltons, CAS 9003-014, typical commercial products Noveon K 752, Rohm-Haas Acumer 1000); CAS 97953-25-8, (typical commercial products Noveon K 775, Rohm-Haas Acumer 2000); AA/SA/SSS polyacrylic terpolymer (an acrylic-acrylamide/sulfonic-styrene sulfonate terpolymer, CAS 151066-66-5, typical commercial products Noveon K 798, Rohm-Haas Acumer 3100); AMP phosphonate (aminotrimethylene phosphonic acid, CAS 6419-19-8, typical commercial product Rhodia Briquest 301-50A); and HEDPA phosphonic acid (a hydroxyethylidene diphosphonic acid, CAS 2809-21-4, typical commercial product Rhodia Briquest ADPA-60AW).

According to various embodiments, a colorant can be added to an alkaline cooling water treatment agent. A typical alkaline treatment agent composition can have a pH of from about 12.0 to about 13.5. An alkaline treatment agent used in the water treatment compositions containing from about 30% to about 75% soft water can comprise one or more of the following components in the stated ranges and can have a final pH range of from about 12.0 to about 13.5:
potassium hydroxide: 19 to 25%;
Polyacrylic acid, (mw 2000): 2 to 25%;
AA/AMPS polyacrylic acid copolymer: 2 to 25%;
AA/SA/SSS polyacrylic acid terpolymer: 2 to 25%;
AMP phosphonic acid: 2 to 25%;
HEDPA phosphonic acid: 2 to 25%;
PBCT phosphonic acid: 2 to 25%;
sodium tolytriazole (50%): 1 to 5%.
It will be understood that this and other water treatment compositions described herein indicate "active" amounts for all the listed ingredients other than soft water. The amount of soft water is a total amount based on sources of water in the formulations.

To this alkaline composition can be added a visible-light detectable colorant, such as, for example, quad sulfonated copper phthalocyanine, commercially available as "Turquoise 8 GL" or "Turquoise NFBL" from American Dyestuff Corporation, Clifton, N.J. The colorant can be added in an amount so that the product has a concentration that contains from about 0.25 to about 3.0 mg/L of colorant. In some embodiments the Turquoise 8 GL can be added in an amount to achieve a final concentration of from about 1.0 to about 2.0 mg/L of the colorant.

In one particular embodiment, the cooling water treatment composition has a pH of 9 or more, and comprises, on a weight percent basis:
 from about 30% to about 75% soft water;
 from about 8% to about 12% alkaline hydroxide;
 from about 2% to about 25% polyacrylic acid component;
 from about 2% to about 25% phosphonic acid component;
 from about 0.5% to about 2.5% azole component; and
 from about 0.1% to about 5%, for example, from about 0.7% to about 2% of the colorant.

In another exemplary embodiment, the cooling water treatment composition can have a pH of from about 12 to about 13.5, and can comprise, on a weight percent basis:
 from about 30% to about 75% soft water;
 from about 8% to about 12% alkaline hydroxide;
 from about 2% to about 25% total polyacrylic acid selected from the group consisting of polyacrylic acid, polyacrylic acid copolymer, polyacrylic acid terpolymer, and combinations thereof;
 from about 2% to about 25% total phosphonic acid selected from the group consisting of AMP phosphonic acid, HEDPA phosphonic acid, PBCT phosphonic acid, and combinations thereof;
 from about 0.5% to about 2.5% total azole selected from the group consisting of a tolytriazole compound, a benzotriazole compound, a mercaptobenzothiazole compound, and combinations thereof; and
 from about 0.1% to about 5%, for example, from about 0.7% to about 2% colorant.

According to various embodiments, the water treatment composition or product can comprise an acidic treatment agent (that is, has a final pH of from about 2.0 to about 5.5) and a colorant. For example, a typical acidic product composition containing from about 30% to about 60% by weight water, can comprise one or more of the following treatment agents (in percent by weight):
 sodium hydroxide: 3.5 to 11%;
 AMP phosphonic acid: 4 to 12%;
 polyacrylic acid (2000 mw): 4 to 12%; and
 AA/AMPS acrylic acid copolymer: 4 to 12%.

To this acidic composition an organic colorant can be added, for example, triphenylmethane, (commercially available as "Acid Blue 9"). The colorant can be added in an amount so that a usable concentration of the product can contain from about 0.12 to about 3.0 mg/L colorant. In some embodiments the product can have a concentration of from about 0.5 mg/L to about 1.0 mg/L colorant.

In an exemplary embodiment, the cooling water treatment composition has a pH of less than 9, and comprises, on a weight percent basis:
 from about 30% to about 60% soft water;
 from about 1.5% to about 6% alkaline hydroxide;
 from about 4% to about 12% polyacrylic acid component;
 from about 4% to about 12% phosphonic acid component; and
 from about 0.1 to about 5%, for example, from about 0.7% to about 2% of the colorant.

In another exemplary embodiment, the cooling water treatment composition has a pH of about 2 to about 5.5, and comprises, on a weight percent basis:
 from about 30% to about 60% soft water;
 from about 1.5% to about 6% alkaline hydroxide;
 from about 4% to about 12% total polyacrylic acid selected from the group consisting of polyacrylic acid, polyacrylic acid copolymer, polyacrylic acid terpolymer, and combinations thereof;
 from about 4% to about 12% total phosphonic acid selected from the group consisting of AMP phosphonic acid, HEDPA phosphonic acid, PBCT phosphonic acid, and combinations thereof; and
 from about 0.1 to about 5%, for example, from about 0.7% to about 2%, colorant.

Experiments have confirmed that Acid Blue 9 can become unstable in alkaline (pH above 9.0) conditions. In alkaline conditions, Acid Blue 9 can react to form various compounds which have absorbances outside of the desired 580 to 640 nm range. According to some embodiments Acid Blue 9 is used in a treatment composition having a pH of less that 9.0.

Products can manufactured in batches of from about 5 gallons to about to 1500 gallons total volume in stirred stainless steel jacketed vessels, FRP vessels, or plastic vessels equipped with internal heat exchange coils. Cooling can be applied during the manufacturing process due to the amount of heat generated via reaction of the various components. In some embodiments, the various components of the water treatment product can be added to the reactor in the orders given in the product composition listings described above. This order of addition can prevent unwanted degradation and precipitation.

Treatment Methods and Systems.

According to various embodiments, the present teachings comprise a system and method for automatically dosing a cooling water treatment product into a water cooling system. As depicted in FIG. 1, a water coolant system 100 can comprise a water cooling apparatus 102, for example, a water cooling tower. Coolant water 114, that contains the treatment composition or product exemplified herein, circulates through pipes or conduits 116 (shown in part) that also provide fluid communication with a spectrophotometer 104. The spectrophotometer 104 comprises a flow-through cell 106 that is provided with an output signal from the spectrophotometer 104 and that is interfaced to an appropriate control circuit 108 to signal an electromagnetic chemical pump 110 when to add fresh additional water treatment product 118 stored in a supply container 112. Additional product 118 can be added when the level of colorant, and hence the level of water treatment product, in the treated system 100, is detected to have decreased below a set control limit. Although FIG. 1 illustrates a single point of introduction 119 for the addition of fresh water treatment product into the water coolant system 100, multiple points can be provided, for example, at different convenient locations within the water coolant system 100.

The level of colorant can be field determined for manual dosage control in the treated water by use of a portable, hand held, solid-state laser diode-based absorbance spectrometer. The spectrometer can be set at a wavelength of from about 580 nm to about 640 nm. In some embodiments, the spectrometer can be set to about 630 nm. An exemplary portable spectrometer can be, for example, a Model 942-620 Blue-Trace™ as manufactured by Orbeco Analytical Systems™, Farmingdale, N.Y.

In use, the amount of product in the treated cooling water can be determined by a calculation based on the known amount and concentration of colorant in the product as manufactured. For example, the colorant can be provided and maintained in a known concentration in the cooling water treatment composition (supply). Therefore, the concentration of the water treatment composition in coolant water can be ascertained in real-time based on measurement of an optical property, such as visible light absorption, at a prescribed discrete wavelength, of the colorant in the water. The absorption parameter value for the colorant can be pre-correlated to the concentration of the water treatment composition in water, for example, by a pre-development of a calibration model that relates measured absorption values associated with the colorant to product concentrations for a similar system. The calibration model, which may be a mathematically curve-fit model, can be referenced in conjunction with on-site or in-the-field measurements taken to determine if the product concentration predicted from the calibration model (based on the measured value of the optical property of the colorant) is different than a predetermined specified target value or range thereof. If different, then additional product can be dosed from the product supply into the treated water of the water coolant system. The coolant level can be intermittently or continuously monitored in this manner, and product dosing can be controlled in conjunction therewith, to maintain the product concentration at a target value or within a target range.

Products containing colorant are usable for control of scale, corrosion, and deposition in a wide variety of commercial and industrial cooling systems. Exemplary systems include, but are not limited to, one pass systems, closed recirculating systems, and open recirculating systems. As an example, such cooling systems are commonly found in schools, hospitals, plastic moulding plants, glass manufacturing plants, chemical plants, steel mills, and die casting plants.

By use of an installed absorbance spectrometer interfaced with a control circuit and chemical feed pump, product level in a cooling water system can be automated based upon the measured amount of colorant present in the treated cooling water.

According to various embodiments, the colorant level in the treated water can be determined by a simple, accurate absorbance spectrophotometer test to control dosage of the product in commercial and industrial cooling systems by either manual or automatic addition to maintain desired control levels.

An exemplary method comprises:
selecting the specific product composition required for the cooling system to be treated. An exemplary alkaline composition can comprise:
soft water −53.68%;
potassium hydroxide 45%-19.5%;
AMP phosphonic acid 50%-8.0%;
polyacrylic acid, 200 mw, 62.2%-12.9%;
sodium tolytriazole 50%-4.6%;
Turquoise 8 GL −1.32%.

According to various embodiments, the composition can be selected to give a working range of from about 100 to about 200 mg/L in the treated water, with a resultant Turquoise 8 GL level of from about 1.32 to about 2.64 mg/L in the treated water. This composition is given as an example, and the range of potential compositions includes those that contain all actives and stabilizers used as well.

The composition noted above can be charged into a jacketed stainless steel kettle of 150 gallon capacity to manufacture a 55 gallon amount of finished product. Following about 30 minutes of blending and cooling, the product can be recovered and placed in a 55 gallon drum for shipment to a point of use.

Product is typically dosed into a cooling water using small electromagnetic pumps controlled by either operation of the cooling system bleed valve or the makeup water meter. Other devices that can be used include timed additions and operation controlled by a blowdown water meter. Testing of the product level in the treated water can be used to ascertain the proper settings for the pumps and to assure continued correct dosage. For the product just described containing 1.32% Turquoise 8 GL, an exemplary level would be from about 100 to about 200 mg/L as product.

Control testing can be undertaken using a portable fixed, or variable, wavelength spectrophotometer. An exemplary test instrument is a Model 942-ABS-620 spectrophotometer as manufactured by Orbeco Analytical Systems of Farmingdale, N.Y. Testing has shown that the use of the specified spectrometer operated at a wavelength of 620 nm results in an absorption of 0.08 at 100 mg/L product (1.32 mg/L Turquoise 8 GL) and 0.16 at 200 mg/L product (2.64 mg/L Turquoise 8 GL) levels in treated cooling water.

Mathematically, a calculation of the concentration (in mg/L) of product present can be performed by multiplying the measured absorption by 1250. If the product is thus determined to be present in a concentration of less than 100 mg/L, the product feed rate is increased. If the product is found to be present at a concentration of more than 200 mg/L, the product feed rate is decreased.

The product can be dosed into commercial and industrial cooling water systems at levels of, for example, 5 to 500 mg/L, for example, 100 to 200 mg/L, to control scale, corrosion, and deposition. Dosage levels can be controlled based on the results obtained by the methods noted above.

It has been further discovered that the two colorants specified are resistant to the action of halogen biocides that are used for control of biological activity in cooling systems. Further, these colorants have been found to be completely unreactive towards all the active ingredients commonly used in cooling water treatment formulations and all constituents commonly present in cooling waters.

Acidic product formulations can be manufactured and tested in the same manner, Acid Blue 9 at exemplary levels of 0.5 to 1.0 mg/L can be used to replace the Turquoise 8 GL.

From the foregoing, it will be observed that numerous modifications and variations can be affected without departing from the present teachings. It is to be understood that no limitation with respect to the specific embodiments illustrated herein is intended or should be inferred.

What is claimed is:

1. A cooling water treatment composition comprising:
  a) at least one water treatment agent selected from the group consisting of a scale inhibitor, a corrosion inhibitor, a deposition inhibitor, a biological organism inhibitor, and combinations thereof; and
  b) a water-soluble colorant tracer that is optically detectable by absorbance at from about 580 nm to about 640 nm, is chemically inert relative to the water treatment agent, and is present in an amount of from about 0.7% by weight solids to about 2% by weight solids based on the total solids weight of the cooling water treatment composition, and comprises a tetra-hydrophilic group-substituted copper porphyrin, or a salt thereof, wherein each hydrophilic group is sulfoxy.

2. The cooling water treatment composition of claim 1, comprising, on a solids weight percent basis:
  from about 30% to about 75% water;
  from about 8% to about 12% alkaline hydroxide;
  from about 2% to about 25% polyacrylic acid component;
  from about 2% to about 25% phosphonic acid component;
  from about 0.5% to about 2.5% azole component;
  from about 0.7% to about 2% of the colorant tracer, and
  wherein the composition has a pH of 9 or more.

3. The cooling water treatment composition of claim 1, comprising, on a solids weight percent basis:
  from about 30% to about 75% water;
  from about 8% to about 12% alkaline hydroxide;
  from about 2% to about 25% total polyacrylic acid selected from the group consisting of polyacrylic acid, polyacrylic acid copolymer, polyacrylic acid terpolymer, and combinations thereof;
  from about 2% to about 25% total phosphonic acid selected from the group consisting of AMP phosphonic acid, HEDPA phosphonic acid, PBCT phosphonic acid, and combinations thereof;
  from about 0.5% to about 2.5% total azole component selected from the group consisting of a tolytriazole compound, a benzotriazole compound, a mercaptobenzothiazole compound, and any combination thereof;
  from about 0.7% to about 2% of the colorant tracer, and
  wherein the composition has a pH of about 12 to about 13.5.

4. The cooling water treatment composition of claim 1, comprising, on a solids weight percent basis:
  from about 30% to about 60% water;
  from about 1.5% to about 6% alkaline hydroxide;
  from about 4% to about 12% polyacrylic acid component;
  from about 4% to about 12% phosphonic acid component;
  from about 0.7% to about 2% of the colorant tracer, and
  wherein the composition has a pH of less than 9.

5. The cooling water treatment composition of claim 1, comprising, on a solids weight percent basis:
  from about 30% to about 60% water;
  from about 1.5% to about 6% alkaline hydroxide;
  from about 4% to about 12% total polyacrylic acid component selected from the group consisting of polyacrylic acid, polyacrylic acid copolymer, polyacrylic acid terpolymer, and combinations thereof;
  from about 4% to about 12% total phosphonic acid selected from the group consisting of AMP phosphonic acid, HEDPA phosphonic acid, PBCT phosphonic acid, and combinations thereof;
  from about 0.7% to about 2% of the colorant tracer, and
  wherein the composition has a pH of about 2 to about 5.5.

6. A method of treating a coolant water system with a water treatment composition, comprising:
  (a) introducing a water treatment composition into water of a coolant water system, said water treatment composition comprising
    at least one water treatment agent selected from the group consisting of a scale inhibitor, a corrosion inhibitor, a deposition inhibitor, a biological organism inhibitor, and a combination thereof, and
    a water-soluble colorant tracer that is optically detectable by absorbance at from about 580 nm to about 640 nm, is chemically inert relative to the water treatment agent, and comprises a tetra-hydrophilic group-substituted copper porphyrin, or a salt thereof, wherein each hydrophilic group is sulfoxy; and
  (b) maintaining the water treatment composition in said water of the coolant water system within a predetermined concentration range using measurement of said absorbance of said tracer of the coolant.

7. The method of claim 6, wherein (b) further comprises:
  i) measuring said absorbance of the colorant tracer present in the water of the water coolant system at a wavelength in the range of about 580 nm to about 640 nm;
  ii) comparing the measured value of the absorbance to a predetermined set control limit value or range thereof; and
  iii) adjusting the concentration of the water treatment composition in the water of the coolant system when the measured value of the absorbance is at or below the set control limit value or range thereof.

8. The method of claim 7, further comprising: iv) repeating steps i), ii), and iii), at least once, wherein the measuring wavelength used in i) is approximately the same value in each repetition.

9. The method of claim 6, further comprising:
  i) providing a fresh water treatment composition supply;
  ii) providing at least one point of introduction into pipes or conduits through which the water flows and is recirculated in the coolant water system, for introducing fresh water treatment composition provided from the supply;
  iii) providing at least one sampling location where the water in the coolant water system is subjected to spectrophotometric analysis with a spectrometer to measure an optical property as absorbance of the water; and iv) providing a controller operable to automatically control introduction of, or display to or alert an operator of the need to manually introduce, additional fresh water treatment composition into the coolant water system from the supply based on the measured value of the optical property as absorbance.

10. The method of claim 9, wherein the spectrometer comprises a portable spectrophotometer.

11. The method of claim 9, wherein the pipes or conduits recirculate the water to cool a reactor vessel.

12. The method of claim 6, further comprising:
i) providing a supply of fresh water treatment composition;
ii) and at least one point of introduction into pipes or conduits through which the water flows and is recirculated in the coolant water system, for introducing fresh water treatment composition from the supply;
iii) providing a feed pump for pumping the fresh water treatment composition from the supply to the point of introduction;
iv) providing at least one sampling location where the water in the coolant water system is subjected to spectrophotometric analysis with an installed, stationary spectrometer to measure an optical property as absorbance of the water; and
v) providing a controller including control circuitry in communication with the feed pump, said controller operable to automatically control introduction of additional fresh water treatment composition into the coolant water system from the supply based on measurement of the absorbance of the colorant tracer in the water of the coolant system.

13. The method of claim 6, wherein the water treatment composition comprises, on a solids weight percent basis:
from about 30% to about 75% water;
from about 8% to about 12% alkaline hydroxide;
from about 2% to about 25% polyacrylic acid component;
from about 2% to about 25% phosphonic acid component;
from about 0.5% to about 2.5% azole component;
from about 0.7% to about 2% of the colorant tracer, and
wherein the composition has a pH of 9 or more and the water treatment composition is maintained in said water of the coolant water system within a concentration range of 0.25 to 3.0 mg/L.

14. The method of claim 6, wherein the water treatment composition comprises, on a solids weight percent basis:
from about 30% to about 75% water;
from about 8% to about 12% alkaline hydroxide;
from about 2% to about 25% total polyacrylic acid selected from the group consisting of polyacrylic acid, polyacrylic acid copolymer, polyacrylic acid terpolymer, and combinations thereof;
from about 2% to about 25% total phosphonic acid selected from the group consisting of AMP phosphonic acid, HEDPA phosphonic acid, PBCT phosphonic acid, and combinations thereof;
from about 0.5% to about 2.5% total azole component selected from the group consisting of a tolytriazole compound, a benzotriazole compound, a mercaptobenzothiazole compound, and any combination thereof;
from about 0.7% to about 2% of the colorant tracer, and
wherein the composition has a pH of about 12 to about 13.5 and the water treatment composition is maintained in said water of the coolant water system within a concentration range of 1.0 to 2.0 mg/L.

15. The method of claim 6, wherein the water treatment composition comprises, on a solids weight percent basis:
from about 30% to about 60% water;
from about 1.5% to about 6% alkaline hydroxide;
from about 4% to about 12% polyacrylic acid component;
from about 4% to about 12% phosphonic acid component;
from about 0.7% to about 2% of the colorant tracer, and
wherein the composition has a pH of less than 9 and wherein the water treatment composition is maintained in said water of the coolant water system within a concentration range of 0.12 to 3.0 mg/L.

16. The method of claim 6, wherein the water treatment composition comprises, on a solids weight percent basis:
from about 30% to about 60% water;
from about 1.5% to about 6% alkaline hydroxide;
from about 4% to about 12% total polyacrylic acid selected from the group consisting of polyacrylic acid, polyacrylic acid copolymer, polyacrylic acid terpolymer, and combinations thereof;
from about 4% to about 12% total phosphonic acid selected from the group consisting of AMP phosphonic acid, HEDPA phosphonic acid, PBCT phosphonic acid, and combinations thereof;
from about 0.7% to about 2% of the colorant tracer, and
wherein the composition has a pH of about 2 to about 5.5 and wherein the water treatment composition is maintained in said water of the coolant water system within a concentration range of 0.5 to 1.0 mg/L.

17. The method of claim 6, wherein the using a measurement of said absorbance comprises using light absorption values at a discrete wavelength.

18. The method of claim 17, wherein the discrete wavelength is 620 nm.

19. The method of claim 6, wherein the water-soluble colorant tracer is optically detectable by absorbance at 620 nm, and wherein (b) further comprises:
i) measuring said optical property as absorbance of the colorant tracer present in the water of the water coolant system wherein said measuring comprises subjecting the water to spectrophotometric analysis with a spectrometer operated at a wavelength of 620 nm;
ii) comparing the measured value of the absorbance to a predetermined set control limit value or range thereof; and
iii) adjusting the concentration of the water treatment composition in the water of the coolant system when the measured value of the absorbance is at or below the set control limit value or range thereof.

* * * * *